United States Patent
Kitamura (10) Patent No.: US 8,494,242 B2
(45) Date of Patent: Jul. 23, 2013

(54) MEDICAL IMAGE MANAGEMENT APPARATUS AND METHOD, AND RECORDING MEDIUM

(75) Inventor: Yoshiro Kitamura, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 626 days.

(21) Appl. No.: 12/760,348

(22) Filed: Apr. 14, 2010

(65) Prior Publication Data

US 2010/0266184 A1    Oct. 21, 2010

(30) Foreign Application Priority Data

Apr. 15, 2009  (JP) ................. 2009/098703
Mar. 23, 2010  (JP) ................. 2010/065811

(51) Int. Cl.
*G06K 9/00*  (2006.01)
(52) U.S. Cl.
USPC ........................... 382/131; 382/128
(58) Field of Classification Search
USPC .................................. 382/128, 131
See application file for complete search history.

(56) References Cited

U.S. PATENT DOCUMENTS

| 8,150,121 B2 * | 4/2012 | Gindele et al. ........... 382/128 |
| 2006/0267976 A1 | 11/2006 | Saito et al. |
| 2008/0267481 A1 * | 10/2008 | Nakamura ............... 382/131 |

* cited by examiner

*Primary Examiner* — Michelle Le
(74) *Attorney, Agent, or Firm* — Sughrue Mion, PLLC

(57) ABSTRACT

A medical-image management apparatus includes: an information obtainment means that obtains information representing a region of a subject represented in a three-dimensional image constructed based on a plurality of slice images captured by a medical-image imaging apparatus, the plurality of slice images being adjacent to each other in a predetermined direction; a reconstruction means that reconstructs, based on the information obtained by the information obtainment means, a plurality of slice images from the three-dimensional image, the plurality of slice images being adjacent to each other in a direction that has been correlated with the region in advance; a recording means that records the plurality of slice images reconstructed by the reconstruction means; and a distribution control means that sequentially distributes, in response to a distribution request for the three-dimensional image input from an external terminal, the plurality of reconstructed slice images from the recording means to the external terminal.

20 Claims, 3 Drawing Sheets

MEDICAL IMAGE MANAGEMENT APPARATUS AND METHOD, AND RECORDING MEDIUM

BACKGROUND OF THE INVENTION

1. Field of the Invention

The present invention relates to a medical image management apparatus, a medical image management method and a recording medium stored therein a program for managing images that have been captured by a medical image imaging apparatus, which images a subject.

2. Description of the Related Art

In recent years, a medical image storage communication system (PACS: Picture Archiving and Communication System) has been used. In the PACS, image data generated by a medical image imaging apparatus, such as a CT apparatus, an MRI apparatus, and an echography apparatus (ultrasonography apparatus), is stored in a management server so that image data corresponding to a distribution request input from a client terminal, such as a medical image display apparatus, can be transferred.

In the medical image imaging apparatus, such as the CT apparatus, a multiplicity of slice images are generated by using a helical scan method that can continuously capture slice images of a subject by imaging. The slice planes of the multiplicity of slice images are perpendicular to the body axis (the slice planes are axial planes), and the generated slice images are sent to a management server. An operator who performs image diagnosis or the like at a client terminal sequentially obtains the multiplicity of slice images generated by the medical image imaging apparatus from the management server. Further, the operator reconstructs, from a three-dimensional image composed of the multiplicity of slice images, slice images of slice planes in a direction corresponding to the region of the subject represented in the three-dimensional image, and displays the reconstructed slice images. Further, the operator performs projection processing on the three-dimensional image to generate a pseudo three-dimensional image, and displays the pseudo three-dimensional image.

Recently, as a medical image imaging apparatus that can acquire high-density slice image data at high speed has become widely used, precise projection data about the subject can be collected. However, the amount of generated image data has increased, and the time period necessary for transfer and reconstruction has become long. Therefore, there is a problem that a response to an image request by the operator is delayed.

Ordinarily, a management server stores a plurality of slice images (axial images) generated by a medical image imaging apparatus. The plurality of slice images are generated by imaging the subject with respect to axial planes of the subject. The management server sequentially distributes the stored axial images in response to a distribution request input from a client terminal. Accordingly, when axial images are displayed as initial images at the client terminal, it is possible to sequentially display each of the axial images in the order of receipt thereof without waiting until transfer of all of the axial images is completed. Therefore, a time lag between the time of sending a request for a desired image to the management server and the time of displaying the image on the display screen is relatively small.

Meanwhile, for example, in diagnosis of a chest image, coronal images are often used, because the slice direction of the coronal images is similar to the direction of an image obtained by general X-ray radiography. When a coronal image, instead of the axial image, is displayed as an initial image, it is possible to improve the efficiency of diagnosis. However, when a slice image of a slice plane (for example, a coronal plane and a sagittal plane) other than the axial plane is displayed as an initial image at the client terminal, at least a part of data representing each of all the axial images is used to generate the slice image. Therefore, it is impossible to display a desirable slice image until transfer of all of the axial images is completed. Hence, the time lag is large.

Meanwhile, U.S. Patent Application Publication No. 20060267976 (Patent Document 1) proposes a method for reducing the delay of display. In the method, image data is stored in a management server as compressed image data. Further, when a client terminal requests voxel data that is necessary to generate a desirable image, compressed image data for restoring the requested voxel data is provided. The client terminal decompresses the provided compressed image data, and generates and displays a desirable image.

However, in the method disclosed in Patent Document 1, a user needs to perform a complex operation for specifying how the image should be displayed. Further, the compressed data that has been sequentially transferred in response to the specification operation by the user needs to be decompressed, and an image is generated from the decompressed voxel data. Therefore, a time lag is generated between the request for the image and the display of the image.

SUMMARY OF THE INVENTION

In view of the foregoing circumstances, it is an object of the present invention to provide a medical image management apparatus and method that can provide, in response to a request for a three-dimensional image from an external terminal, an initial image appropriate for observation of a region of a subject represented by the three-dimensional image with excellent response. Further, it is another object of the present invention to provide a recording medium stored therein a program for managing medical images.

A medical image management apparatus of the present invention is a medical image management apparatus for managing images of a subject that have been imaged by a medical image imaging apparatus, the medical image management apparatus comprising:

an information obtainment means that obtains information representing a region of the subject represented in a three-dimensional image constructed based on a plurality of slice images that have been captured by the medical image imaging apparatus, the plurality of slice images being adjacent to each other in a predetermined direction;

a reconstruction means that reconstructs, based on the information representing the region obtained by the information obtainment means, a plurality of slice images from the three-dimensional image, the plurality of slice images being adjacent to each other in a direction that has been correlated with the region (or related to the region) in advance;

a recording means that records the plurality of slice images reconstructed by the reconstruction means; and a distribution control means that sequentially distributes, in response to a distribution request for the three-dimensional image input from an external terminal, the plurality of reconstructed slice images from the recording means to the external terminal.

The direction that has been correlated with the region in advance may include the predetermined direction.

The distribution request for the three-dimensional image input or sent from the external terminal does not specify the direction in which the plurality of slice image composing the three-dimensional image are adjacent to each other.

A region of a subject represented in an image may include a combination of a plurality of regions. Therefore, when the number of regions is one, the direction that has been correlated with the one region in advance is the direction that has been correlated with the region. When the number of regions is two or greater, the direction that has been correlated with a combination of the two or greater regions in advance is the direction that has been correlated with the region.

In the above apparatus, when the position of a lesion in the three-dimensional image has been correlated with the three-dimensional image, the distribution control means may give priority to distribution of a reconstructed slice image including the position of the lesion over distribution of the other slice images of the plurality of reconstructed slice images.

When a reading report that records a specific position in the three-dimensional image is correlated with the three-dimensional image, the distribution control means may give priority to distribution of a reconstructed slice image including the specific position over distribution of the other slice images of the plurality of reconstructed slice images.

The information obtainment means may obtain, with respect to a plurality of three-dimensional images obtained by imaging the same region of the subject at a plurality of different points of time, information representing a region of the subject represented in the plurality of three-dimensional images. The reconstruction means may reconstruct, based on the information representing the region obtained by the information obtainment means, a plurality of slice images that are adjacent to each other in a direction that has been correlated with the region in advance from each of the plurality of three-dimensional images. Further, the distribution control means may sequentially distribute, based on a distribution request for the plurality of three-dimensional images, the plurality of reconstructed slice images in such a manner that slice images representing the same slice plane in the plurality of three-dimensional images are distributed together.

When the position of a lesion in at least one of the plurality of three-dimensional images has been correlated with the at least one of the plurality of three-dimensional images, the distribution control means may give priority to distribution of a reconstructed slice image including the position of the lesion over distribution of the other slice images of the plurality of reconstructed slice images.

The reconstruction means may judge whether the direction correlated with the region in advance differs from the predetermined direction, and reconstruct the plurality of slice images only when the correlated direction differs from the predetermined direction.

When the subject is a human body, and the predetermined direction is an axial direction, if the information obtained by the information obtainment means represents the thorax of the subject, or the abdomen of the subject, or the lower limb or limbs of the subject, or the thorax and the thoracoabdomen of the subject, or the abdomen and the pelvis of the subject, the reconstruction means may reconstruct a plurality of coronal images that are adjacent to each other from the three-dimensional image. If the information obtained by the information obtainment means represents a region from the head to the neck of the subject or from the thorax to the abdomen of the subject, the region including at least one of vertebrae of the subject, or a joint region of the subject, the reconstruction means may reconstruct a plurality of sagittal images that are adjacent to each other from the three-dimensional image. If the information obtained by the information obtainment means represents the torso of the subject, or at least one of the urinary organs of the subject, or the pituitary gland of the subject, the reconstruction means may reconstruct a plurality of coronal images or sagittal images that are adjacent to each other from the three-dimensional image.

The information obtainment means may automatically obtain the information representing the region by performing image analysis on the three-dimensional image or at least one of the slice images composing the three-dimensional image. Alternatively, the information obtainment means may automatically obtain the information representing the region based on subject information provided, as supplementary information, for at least one of the slice images composing the three-dimensional image.

A medical image management system of the present invention is a medical image management system comprising:

the medical image management apparatus; and an external terminal, wherein the external terminal includes a sending/receiving means that outputs a distribution request for the three-dimensional image to the medical image management apparatus and sequentially receives a plurality of slice images distributed from the medical image management apparatus, an image display means for displaying an image, and a display control means that displays, as an initial image, one of the plurality of slice images received by the sending/receiving means on the image display means.

A medical image management method of the present invention is a medical image management method for managing images of a subject that has been imaged by a medical image imaging apparatus, the method comprising the steps of:

obtaining information representing a region of the subject represented in a three-dimensional image constructed based on a plurality of slice images that have been captured by the medical image imaging apparatus, the plurality of slice images being adjacent to each other in a predetermined direction;

reconstructing, based on the obtained information representing the region, a plurality of slice images from the three-dimensional image, the plurality of slice images being adjacent to each other in a direction that has been correlated with the region in advance;

recording the plurality of reconstructed slice images; and sequentially distributing, in response to a distribution request for the three-dimensional image input from an external terminal, the plurality of reconstructed and recorded slice images to the external terminal.

In the above method, when the position of a lesion in the three-dimensional image has been correlated with the three-dimensional image, priority may be given to distribution of a reconstructed slice image including the position of the lesion over distribution of the other slice images of the plurality of reconstructed slice images.

When a reading report that records a specific position in the three-dimensional image has been correlated with the three-dimensional image, priority may be given to distribution of a reconstructed slice image including the specific position over distribution of the other slice images of the plurality of reconstructed slice images.

With respect to a plurality of three-dimensional images obtained by imaging the same region of the subject at a plurality of different points of time, information representing a region of the subject represented in the plurality of three-dimensional images may be obtained. Further, a plurality of slice images that are adjacent to each other in a direction that has been correlated with the region in advance may be reconstructed from each of the plurality of three-dimensional images based on the obtained information representing the region. Further, the plurality of reconstructed slice images may be sequentially distributed, based on a distribution request for the plurality of three-dimensional images, in such a manner that slice images representing the same slice plane in the plurality of three-dimensional images are distributed together.

When the position of a lesion in at least one of the plurality of three-dimensional images has been correlated with the at least one of the plurality of three-dimensional images, priority may be given to distribution of a reconstructed slice image including the position of the lesion over distribution of the other slice images of the plurality of reconstructed slice images.

A recording medium stored therein a program of the present invention may store a program for managing images of a subject that has been imaged by a medical image imaging apparatus, the program causing a computer to execute the procedures of:

obtaining information representing a region of the subject represented in a three-dimensional image constructed based on a plurality of slice images that have been captured by the medical image imaging apparatus, the plurality of slice images being adjacent to each other in a predetermined direction;

reconstructing, based on the obtained information representing the region, a plurality of slice images from the three-dimensional image, the plurality of slice images being adjacent to each other in a direction that has been correlated with the region in advance;

recording the plurality of reconstructed slice images; and sequentially distributing, in response to a distribution request for the three-dimensional image input from an external terminal, the plurality of reconstructed and recorded slice images to the external terminal.

In the recording medium stored therein the medical image management program, when the position of a lesion in the three-dimensional image has been correlated with the three-dimensional image, priority may be given to distribution of a reconstructed slice image including the position of the lesion over distribution of the other slice images of the plurality of reconstructed slice images.

Further, with respect to a plurality of three-dimensional images obtained by imaging the same region of the subject at a plurality of different points of time, information representing a region of the subject represented in the plurality of three-dimensional images may be obtained. Further, a plurality of slice images that are adjacent to each other in a direction that has been correlated with the region in advance may be reconstructed from each of the plurality of three-dimensional images based on the obtained information representing the region. Further, the plurality of reconstructed slice images may be sequentially distributed, based on a distribution request for the plurality of three-dimensional images, in such a manner that slice images representing the same slice plane in the plurality of three-dimensional images are distributed together.

According to the medical image management method and apparatus and the recording medium stored therein a program of the present invention, information representing a region of a subject represented in a three-dimensional image constructed based on a plurality of slice images that have been captured by a medical image imaging apparatus, the plurality of slice images being adjacent to each other in a predetermined direction, is obtained. Further, a plurality of slice images are reconstructed, based on the obtained information representing the region, from the three-dimensional image, the plurality of slice images being adjacent to each other in a direction that has been correlated with the region in advance. The plurality of reconstructed slice images are recorded. Further, the plurality of reconstructed and recorded slice images are sequentially distributed to an external terminal in response to a distribution request for the three-dimensional image input from the external terminal. Therefore, before a distribution request for a specific three-dimensional image is input from the external terminal, a plurality of slice images can be reconstructed from the three-dimensional image in advance in such a manner that the plurality of slice images are adjacent to each other in a direction that is appropriate for observation of the region of the subject represented in the three-dimensional image. Hence, it is possible to provide, in response to the request for the three-dimensional image from the external terminal, an initial image appropriate for observation of the region of the subject represented in the three-dimensional image with excellent response.

In the method and apparatus and the recording medium stored therein the program, when the position of a lesion in the three-dimensional image has been correlated with the three-dimensional image, if priority is given to distribution of a reconstructed slice image including the position of the lesion over distribution of the other slice images of the plurality of reconstructed slice images, it is possible to provide the slice image including the lesion as an initial image.

When a reading report that records a specific position in the three-dimensional image has been correlated with the three-dimensional image, if priority is given to distribution of a reconstructed slice image including the specific position over distribution of the other slice images of the plurality of reconstructed slice images, it is possible to provide the slice image including the specific position recorded in the reading report as an initial image.

Further, with respect to a plurality of three-dimensional images obtained by imaging the same region of the subject at a plurality of different points of time, when information representing a region of the subject represented in the plurality of three-dimensional images is obtained, and a plurality of slice images that are adjacent to each other in a direction that has been correlated with the region in advance are reconstructed based on the obtained information representing the region, and the plurality of reconstructed slice images are sequentially distributed, based on a distribution request for the plurality of three-dimensional images, in such a manner that slice images representing the same slice plane in the plurality of three-dimensional images are distributed together, at an external terminal to which the slice images are distributed, comparative observation of slice images representing the same slice plane can be started without waiting until transfer of all of the three-dimensional images is completed

DESCRIPTION OF THE PREFERRED EMBODIMENTS

Figure 1:
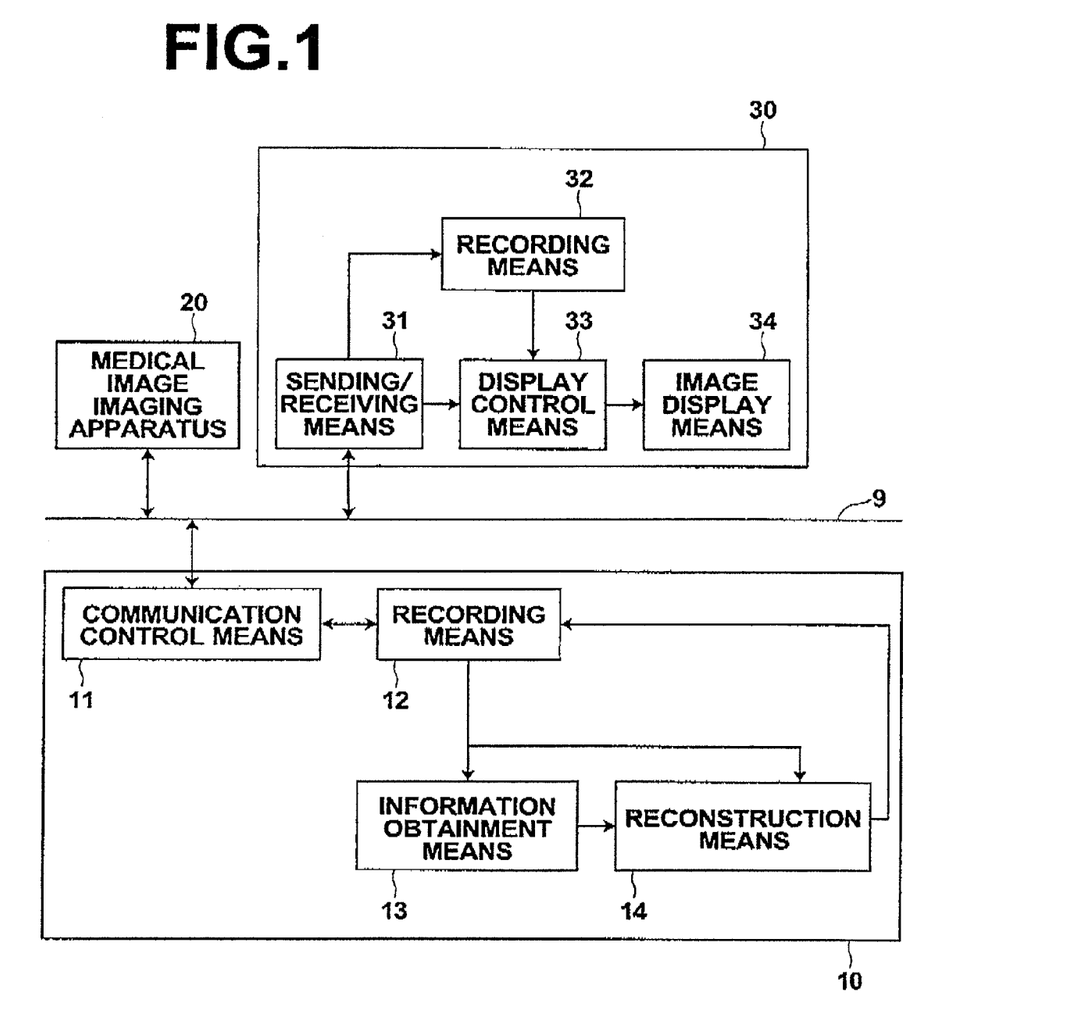
FIG. 1 is a schematic diagram illustrating the configuration of a medical image management system according to an embodiment of the present invention.

Hereinafter, embodiments of the present invention will be described with reference to drawings. FIG. 1 is a schematic block diagram illustrating the configuration of a medical image management system. As illustrated in FIG. 1, the medical image management system includes an image management server 10 (medical image management apparatus), a medical image imaging apparatus 20, a client terminal (external terminal) 30, which are connected to each other through a network 9 so that they can communicate with each other.

The medical image imaging apparatus 20 is, for example, a helical scan X-ray CT apparatus. For example, the helical scan X-ray CT apparatus generates a multiplicity of slice images of slice planes (axial planes) perpendicular to the body axis of a subject (patient), and the multiplicity of slice images are adjacent to each other. Images generated by the medical image imaging apparatus 20 are sent to the image management server 10, and stored in the image management server 10.

In the image management server 10, an image management program for causing a computer to execute image management processing of the present invention, an image processing program for causing a computer to perform various kinds of image processing, and the like are installed. These programs may be stored in a recording medium, such as a DVD and a CD-ROM, and distributed to be installed in a computer from the recording medium. Alternatively, these programs may be stored in a storage device of a server computer connected to a network or in a network storage in such a mariner that the programs are accessible from the outside. The programs may be downloaded and installed in a computer used by a doctor based on a request for downloading.

The image management server 10 obtains, through the network 9, images that have been captured by the medical image imaging apparatus 20, and stores and manages the obtained images. The image management server 10 includes a CPU, a memory, and a hard disk. Further, the image management server 10 is connected to a display and an input device, such as a mouse. The memory stores an image management program. The image management program regulates, as processing to be executed by the CPU, communication control processing (distribution control processing), recording processing, information obtainment processing and reconstruction processing. When the CPU executes these kinds of processing based on the programs, the computer functions as a communication control means 11 (distribution control means), a recording means 12, an information obtainment means 13, and a reconstruction means 14.

The recording means (hard disk) 12 records image data received from the medical image imaging apparatus 20 or the like and image data reconstructed by the reconstruction means 14.

The recording means 12 stores information representing the position of a lesion in an image represented by the image data in such a manner that the information representing the position of the lesion is correlated with the image data. Here, the expression "the information representing the position of the lesion is correlated with the image data" means, for example, a state in which the information about the position of the lesion per se is provided as supplementary information for the three-dimensional image or attached to the three-dimensional image, or a state in which the three-dimensional image is linked to a record destination at which the information about the position is recorded or information about the link to the record destination is provided as supplementary information for the three-dimensional image, or the like.

The information about the position of the lesion may be stored based on an input of the position of a lesion by a doctor or the like. The position of the lesion may be found by the doctor or the like by reading a three-dimensional image, and the information about the position of the lesion may be input at the client terminal 30 or other client terminals or the like by using a pointing device, a keyboard or the like, which is provided in the terminals. Alternatively, an automatic detection result of a lesion by a computer-aided diagnosis (CAD) system may be stored as the information about the position of the lesion. Further, the information about the position of the lesion may represent an arbitrary position within the lesion. Alternatively, the information about the position of the lesion may represent the range of positions of a lesion region.

Further, the recording means 12 stores a reading report that records a specific position in the image represented by the image data in such a manner that the reading report is correlated with the image data. The expression "the reading report is correlated with the image data" means, for example, a state in which the reading report per se is provided as supplementary information for the three-dimensional image or attached to the three-dimensional image, or a state in which the three-dimensional image is linked to a record destination at which the reading report is recorded or information about the link to the record destination is provided as supplementary information for the three-dimensional image, or the like. Here, the term "specific position" is a wide range of position that is specified in the reading report. For example, the "specific position" is the coordinate of the position of the lesion written in the findings by the doctor or the like in the reading report, the range of positions of a region of interest, or the like. For example, the position of a slice plane represented in a reference image attached to the reading report is also the specific position, which is specified in the reading report.

Further, the recording means 12 stores a table, for example, as illustrated in Table 1. In the table, each region of a subject, which is the subject of imaging by the medical image imaging apparatus 20, and a slice plane that is appropriate for observation of an image representing each of the regions are correlated with each other, and stored. Table 1 shows an example of correlation (corresponding relationship) between each region of a human body, which is the subject of imaging, and a slice plane appropriate for observation of an image representing each of the regions.

TABLE 1

| Region | Reconstruction slice plane |
|---|---|
| including region from head to neck + vertebra | sagittal |
| including region from thorax to abdomen + vertebra | sagittal |
| thorax alone, or thorax + thoracoabdomen | coronal |
| abdomen alone, or abdomen + pelvis | coronal |
| substantially not including thorax + extracardiac region | axial |
| entire lower limbs (legs) | coronal |
| substantially not including legs + extraarticular region | sagittal |
| others | axial |

The information obtainment means 13 obtains information representing a region of the subject represented in a three-dimensional image composed of the plurality of axial images received from the medical image imaging apparatus 20 (the information is, for example, a text of the name of the region or a code identifying each region).

Specifically, the information obtainment means 13 recognizes the region of the subject represented in the three-dimensional image by analyzing the image data of the three-dimensional image, and obtains information representing the recognized region. For example, as described in U.S. Patent Application Publication No. 20080267481, each of slice images composing a three-dimensional image is normalized, and a multiplicity of feature values are calculated from the normalized slice images. Further, the feature value calculated for each of the normalized slice images is input to a classifier obtained by AdaBoost, and a score representing a probability of being each region is calculated for each of the regions. Further, the calculated score for each of the regions is used as an input, and a dynamic programming method is used to determine the region represented in each of the slice images in such a manner that when the slice images are arranged from the upper part to the lower part of a human body, the arrangement order of the body parts, namely the head, the head and the neck, the neck, the thorax, the thoracoabdomen, the abdomen, the pelvis, and the legs, is maintained. Accordingly, it becomes possible to recognize regions of the subject represented in the three-dimensional image for each unit of the head, the head and the neck, the neck, the thorax, the thoracoabdomen, the abdomen, the pelvis, and the legs. In addition to the recognition processing, recognition processing may be performed to more precisely recognize a region, such as the vertebra or vertebrae, the heart, and the joint, by using a similar recognition method.

Further, with respect to a plurality of three-dimensional images obtained by imaging the same region of the subject at a plurality of different points of time, which have been received from the medical image imaging apparatus 20, the information obtainment means 13 obtains information representing a region of the subject represented in the plurality of three-dimensional images. For example, the information obtainment means 13 recognizes a region of the subject represented in one of the plurality of three-dimensional images by using a method for analyzing image data as described above. Further, the information obtainment means 13 obtains information representing the recognized region as information representing the region of the subject represented in the plurality of three-dimensional images.

The reconstruction means 14 reconstructs, based on information representing the region of the subject represented in the three-dimensional image, the information being obtained by the information obtainment means 13, a plurality of slice images that are adjacent to each other in a direction that has been correlated with the region in advance. The reconstruction means 14 reconstructs the plurality of slice images from the three-dimensional image composed of a plurality of axial images.

First, the reconstruction means 14 refers to a table showing correlation between each region of the subject, which is the subject of imaging by the medical image imaging apparatus 20, and a slice plane that is appropriate to observe an image including the region. The reconstruction means 14 specifies (identifies) a slice plane correlated with the region of the subject represented in the three-dimensional image with reference to the table. The slice plane is specified based on the information representing the region, which has been obtained by the information obtainment means 13. Further, the reconstruction means 14 judges whether the slice plane correlated with the region differs from an axial plane or not. When the slice plane correlated with the region at least differs from an axial plane, the reconstruction means 14 reconstructs a plurality of slice images of the slice plane correlated with the region. The plurality of slice images are adjacent to each other.

The reconstruction means 14 may perform reconstruction processing on all of three-dimensional images received from the medical image imaging apparatus 20 without regard to whether the correlated slice plane is an axial plane or not. Alternatively, the reconstruction means 14 may perform reconstruction processing only when the correlated slice plane differs from an axial plane.

Figure 2:
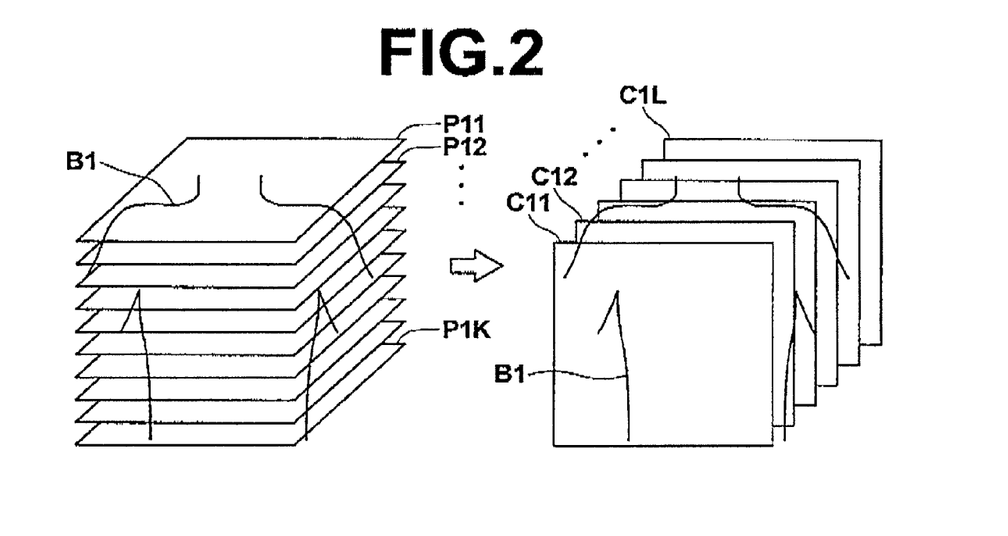
FIG. 2 is a diagram illustrating an example of reconstruction processing by a reconstruction means illustrated in FIG. 1.

For example, when the information obtainment means 13 obtains information indicating that the region of the subject represented in the three-dimensional image is thorax B1, the reconstruction means 14 reconstructs a plurality of coronal images C11, C12, . . . , C1L, which are adjacent to each other, as illustrated in FIG. 2, because in Table 1, the coronal plane is correlated with the thorax region. The reconstruction means 14 reconstructs the plurality of coronal images from the three-dimensional image composed of a plurality of axial images P11, P12, . . . , P1K.

Figure 3:
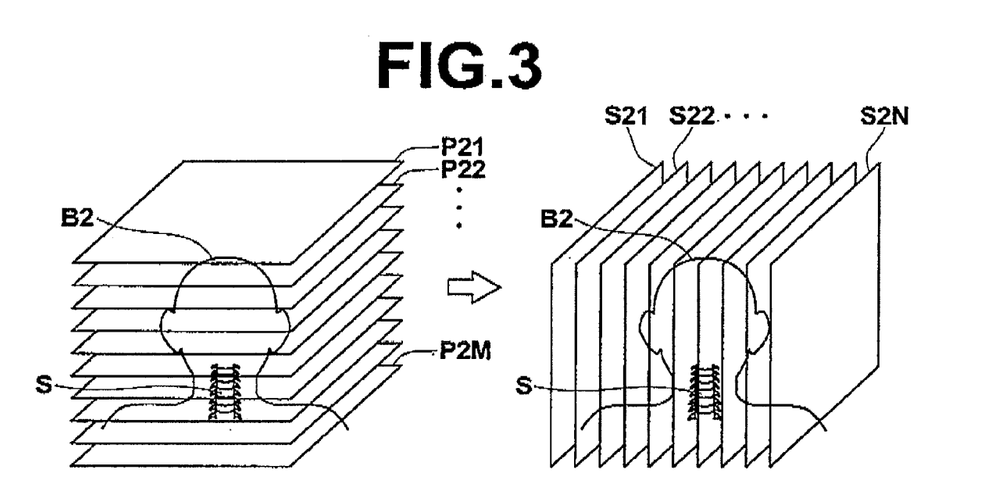
FIG. 3 is a diagram illustrating another example of reconstruction processing by the reconstruction means illustrated in FIG. 1.

When the information obtainment means 13 obtains information indicating that the region of the subject represented in the three-dimensional image is region B2 from the head to the neck including at least one of vertebrae S, the reconstruction means 14 reconstructs a plurality of sagittal images S21, S22, . . . , S2N, which are adjacent to each other, as illustrated in FIG. 3, because in Table 1, the sagittal plane is correlated with the region. The reconstruction means 14 reconstructs the plurality of sagittal images from the three-dimensional image composed of a plurality of axial images P21, P22, . . . , P2M.

When the information obtainment means 13 obtains information indicating that the region of the subject represented in the three-dimensional image is the torso, or at least one of the urinary organs, or the pituitary gland of the subject, the reconstruction means 14 reconstructs a plurality of coronal images or sagittal images, which are adjacent to each other.

In Table 1, the judgment as to whether the extracardiac region is substantially included or not is made based on whether the ratio of the size of the cardiac region to the size of the whole image is greater than a predetermined threshold value or not. Similarly, the judgment as to whether the extraarticular region is substantially included may be made based on whether the ratio of the size of the joint region to the size of the whole image is greater than a predetermined threshold value or not.

The reconstruction means 14 reconstructs, based on the information representing the region obtained by the information obtainment means 13, a plurality of slice images from each of a plurality of three-dimensional images obtained by imaging the same region of the subject at a plurality of different points of time, which have been received from the medical image imaging apparatus 20. The plurality of slice images are reconstructed in such a manner that they are adjacent to each other in a direction that has been correlated with the region in advance. The reconstruction processing may be performed by directly applying the reconstruction processing performed for the single three-dimensional image as described above to the reconstruction processing for the plurality of three-dimensional images.

The communication control means 11 communicates with other apparatuses through the network 9, and sends/receives image data or the like. For example, when the communication control means 11 receives a distribution request for a specific three-dimensional image from the client terminal 30, the communication control means 11 sequentially distributes the image data that has been reconstructed by the reconstruction means 14 as a three-dimensional image from the recording means 12 to the client terminal 30. If reconstructed image data is not present, the communication control means 11 sequentially sends image data that has been received, as the three-dimensional image, from the medical image imaging apparatus 20 or the like.

When the image data the distribution request for which has been received represents a plurality of three-dimensional images obtained by imaging the same region of the subject at a plurality of different points of time, the plurality of reconstructed slice images are sequentially distributed in such a manner that slice images representing the same slice plane in the plurality of three-dimensional images are sent together. Here, the expression "slice images representing the same slice plane" means slice images in which the same slice plane of the subject has been imaged.

When the plurality of three-dimensional images obtained by imaging the same region of the subject at a plurality of different points of time have been obtained by imaging by the medical image imaging apparatus 20 or the like in the same imaging condition, i.e., a condition in which the position of the subject with respect to the imaging apparatus is the same and the thickness of the slice image (the interval of slice images) is the same or the like, a slice image of the same order of arrangement in each of the three-dimensional images tends to represent the same slice plane of the subject in many cases. Therefore, the communication control means 11 sequentially distributes, based on a distribution request for the plurality of three-dimensional images, the plurality of reconstructed slice images in such a manner that slice images of the same order of arrangement in the respective three-dimensional images are sent together.

Figure 4:
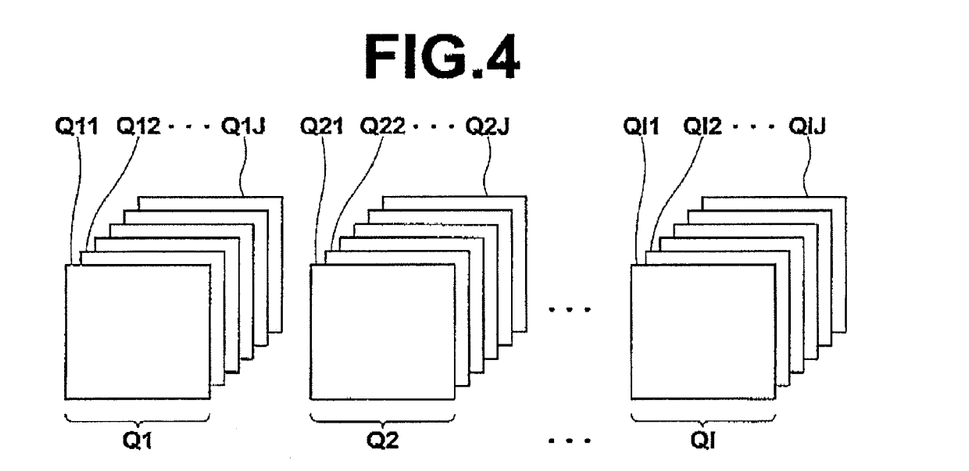
FIG. 4 is a diagram for explaining distribution of a plurality of three-dimensional images.

For example, as illustrated in FIG. 4, when a distribution request for a plurality of three-dimensional images Q1, Q2, ... QI, which were obtained by imaging the same region of the subject at a plurality of different points of time is received, first, slice images Q11, Q21, ... QI1 are distributed. Next, slice images Q12, Q22, ... QI2 are distributed. Next, slice images Q13, Q23, ... QI3 are distributed, and ..., and finally, slice images Q1J, Q2J, ... QIJ are distributed.

Further, the plurality of three-dimensional images obtained by imaging the same region of the subject at a plurality of different points of time may be aligned relative to each other in advance. Further, the plurality of three-dimensional images may be sequentially distributed, based on the distribution request, in such a manner that slice planes at the same positions of the plurality of three-dimensional images are sent together.

Further, when a distribution request for a three-dimensional image is received, if the position of the lesion in the three-dimensional image is correlated with the three-dimensional image, the distribution control means 11 sends slice images of the three-dimensional image to be distributed by giving priority to distribution of a slice image including the position of the lesion over distribution of the other slice images of the three-dimensional image. For example, when information about the position of the lesion is provided as supplementary information for the three-dimensional image the distribution request for which has been received, or when the three-dimensional image is linked to a record destination in which the information about the position of the lesion is stored, the distribution control means 11 distributes the slice image including the position of the lesion first, and sequentially distributes the remaining slice images.

Further, when a distribution request for a three-dimensional image is received, if a reading report that records a specific position in the three-dimensional image is correlated with the three-dimensional image, the distribution control means 11 sends the slice images of the three-dimensional image to be distributed by giving priority to distribution of a slice image including the specific position over distribution of the other slice images of the three-dimensional image.

For example, in FIG. 4, when three-dimensional image Q1 is linked to a reading report that records the position of a lesion in the image, if a slice image including the position of the lesion is slice image Q1J, the communication control means 11 distributes, based on a distribution request for the three-dimensional image Q1 from an external terminal, the slice image Q1J first. Then, after distributing the slice image Q1J, the remaining slice images Q11, Q12, ..., Q1(J−1) are sequentially distributed.

In FIG. 4, when the three-dimensional image Q1 is linked to a reading report that records the position of a lesion in the image, if a slice image including the position of the lesion is slice image Q1J, the communication control means 11 that has received a distribution request for the three-dimensional images Q1, Q2, ..., QI distributes the slice images Q1J, Q2J, ..., QIJ first. Then, after distributing the slice images Q1J, Q2J, ..., QIJ, slice images Q11, Q21, ..., QI1 are distributed. Next, slice images Q12, Q22, ..., QI2 are distributed. Finally, Q1(J−1), Q2(J−1)1, ..., QI(J−1) are distributed.

When a distribution request for a specific three-dimensional image from the client terminal 30 includes specification of the thickness d2 of the slice image (interval of slice images or planes) the communication control means 11 may judge whether the thickness d1 in the slice image represented by image data to be distributed differs from specified thickness d2. If the thickness d1 differs from the specified thickness d2, the reconstruction means 14 reconstructs, as a three-dimensional image to be distributed, a three-dimensional image composed of slice images with the thickness d2. The reconstructed image is distributed.

Figure 5:
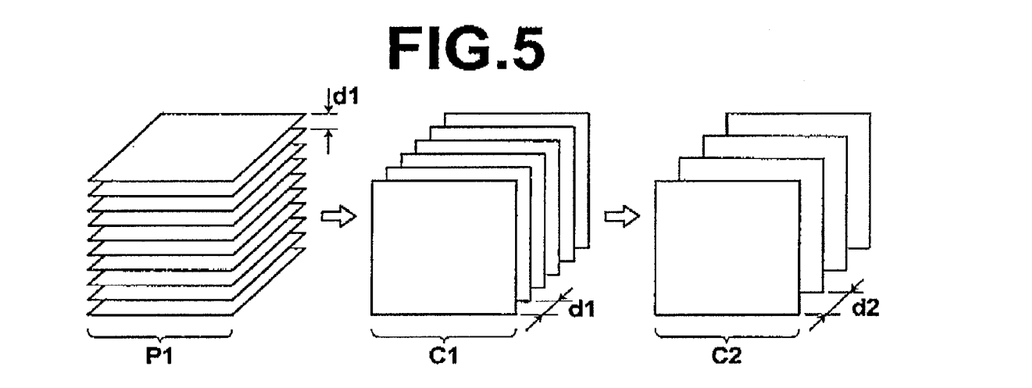
FIG. 5 is a diagram for explaining distribution of a three-dimensional image when a distribution request specifying a thickness is received.

For example, as illustrated in FIG. 5, when the reconstruction means 14 reconstructs a plurality of coronal images C1 with the thickness d1 of slice images from three-dimensional image P1 composed of a plurality of axial images with the thickness d1 of slice images, and the plurality of reconstructed coronal images C1 are recorded in the recording means 12, if a distribution request for the three-dimensional image, the request specifying the thickness d2 (d1≠d2) of slice images, is received, a plurality of coronal images C2 with the thickness d2 of slice images are further reconstructed from the plurality of reconstructed coronal images C1, and the plurality of reconstructed coronal images C2 are distributed.

The client terminal 30 is a medical image display apparatus or the like, which is used by an operator, such as a doctor, to view or observe or browse images or the like. The client terminal 30 outputs, in response to a display instruction of target data input by the operator, a distribution request for a specific three-dimensional image to the image management server 10. The client terminal 30 includes a sending/receiving means 31, a recording means 32, an image display means 34, a display control means 33, and the like. The sending/receiving means 31 outputs a distribution request for a specific three-dimensional image to the image management server 10, and sequentially receives a plurality of slice images distributed from the image management server 10. The recording means 32 records image data received by the sending/receiving means 31. The image display means 34 displays images. The display control means 33 displays, as an initial image, one of the slice image received by the sending/receiving means 31.

Next, the flow of processing by the image management server 10 will be described. First, when the image management server 10 receives a multiplicity of axial images that are adjacent to each other from the medical image imaging apparatus 20, the received image data is recorded in the recording means 12. Then, the information obtainment means 13 obtains information representing the region of the subject represented in the three-dimensional image. Further, the reconstruction means 14 reconstructs a plurality of slice images that are adjacent to each other in a direction that has been correlated with the region in advance. The reconstruction means 14 reconstructs the plurality of slice images based on the information representing the region of the subject represented in the three-dimensional image, the information having been obtained by the image obtainment means 13. The plurality of slice images are reconstructed from the three-dimensional image composed of the plurality of axial images that have been received from the medical image imaging apparatus 20. The plurality of reconstructed slice images are recorded in the recording means 12. After then, when the communication control means 11 receives a distribution request for the three-dimensional image from the client terminal 30, the communication control means 11 sequentially distributes the plurality of reconstructed slice images from the recording means 12 to the client terminal 30.

According to the embodiments, in the image management server 10 that obtains, through the network 9, images that have been captured by the medical image imaging apparatus 20, and stores and manages the images, it is possible to reconstruct a plurality of slice images before a distribution request for a specific three-dimensional image is sent from the client terminal 30. The plurality of slice images are adjacent to each other in a direction appropriate for observation of the region of the subject represented in the image. Therefore, when the client terminal 30 sends a request for a three-dimensional image, it is possible to provide an initial image appropriate for observation of the region of the subject represented in the three-dimensional image with excellent response.

In the above embodiments, a case in which the information representing the region is automatically obtained by performing image analysis on the three-dimensional image or at least one of the slice images composing the three-dimensional image has been described. Alternatively, the information representing the region may be automatically obtained based on subject information provided, as supplementary information, for at least one of the slice images composing the three-dimensional image.

Further, when a distribution request for a three-dimensional image is received, the distribution control means 11 may change an image to be distributed based on the sender of the distribution request. For example, the distribution control means 11 may judge, based on a sender ID included in the distribution request, whether the sender of the distribution request is a radiologist or a clinician (a surgeon or the like). If the sender of the distribution request is a radiologist, an image before reconstruction may be distributed. If the sender of the distribution request is a clinician, an image after reconstruction may be distributed.

What is claimed is:

1. A medical image management apparatus for managing images of a subject that has been imaged by a medical image imaging apparatus, the medical image management apparatus comprising:
    a first recording means that records each region of the subject which is a target of imaging by the medical image apparatus, correlated with a direction for reconstruction;
    an information obtainment means that obtains information representing a region of the subject represented in a three-dimensional image constructed based on a plurality of slice images that have been captured by the medical image imaging apparatus, the plurality of slice images being adjacent to each other in a predetermined direction;
    a reconstruction means that reconstructs the plurality of slice images which are adjacent in the predetermined direction, into a plurality of slice images which are adjacent in a direction correlated with the region of the subject represented by the information obtained by the information obtainment means in the first recording means prior to a request for distribution of the three dimensional image being received from an external terminal;
    a second recording means that records the plurality of slice images reconstructed by the reconstruction means; and
    a distribution control means that sequentially distributes, in response to a distribution request for the three-dimensional image input from an external terminal, the plurality of reconstructed slice images from the recording means to the external terminal.

2. A medical image management apparatus, as defined in claim 1, wherein when the position of a lesion in the three-dimensional image has been correlated with the three-dimensional image, the distribution control means gives priority to distribution of a reconstructed slice image including the position of the lesion over distribution of the other slice images of the plurality of reconstructed slice images.

3. A medical image management apparatus, as defined in claim 1, wherein when a reading report that records a specific position in the three-dimensional image is correlated with the three-dimensional image, the distribution control means gives priority to distribution of a reconstructed slice image including the specific position over distribution of the other slice images of the plurality of reconstructed slice images.

4. A medical image management apparatus, as defined in claim 1, wherein the information obtainment means obtains, with respect to a plurality of three-dimensional images obtained by imaging the same region of the subject at a plurality of different points of time, information representing a region of the subject represented in the plurality of three-dimensional images, and wherein the reconstruction means reconstructs, based on the information representing the region obtained by the information obtainment means, a plurality of slice images that are adjacent to each other in a direction that has been correlated with the region in advance from each of the plurality of three-dimensional images, and wherein the distribution control means sequentially distributes, based on a distribution request for the plurality of three-dimensional images, the plurality of reconstructed slice images in such a manner that slice images representing the same slice plane in the plurality of three-dimensional images are distributed together.

5. A medical image management apparatus, as defined in claim 4, wherein when the position of a lesion in at least one of the plurality of three-dimensional images has been correlated with the at least one of the plurality of three-dimensional images, the distribution control means gives priority to distribution of a reconstructed slice image including the position of the lesion over distribution of the other slice images of the plurality of reconstructed slice images.

6. A medical image management apparatus, as defined in claim 1, wherein the reconstruction means judges whether the correlated direction differs from the predetermined direction, and reconstructs the plurality of slice images only when the correlated direction differs from the predetermined direction.

7. A medical image management apparatus, as defined in claim 1, wherein when the subject is a human body, and the predetermined direction is an axial direction, if the information obtained by the information obtainment means represents the thorax of the subject, or the abdomen of the subject, or the lower limb or limbs of the subject, or the thorax and the thoracoabdomen of the subject, or the abdomen and the pelvis of the subject, the reconstruction means reconstructs a plurality of coronal images that are adjacent to each other from the three-dimensional image.

8. A medical image management apparatus, as defined in claim 1, wherein when the subject is a human body, and the predetermined direction is an axial direction, if the information obtained by the information obtainment means represents a region from the head to the neck of the subject or from the thorax to the abdomen of the subject, the region including at least one of vertebrae of the subject, or a joint region of the subject, the reconstruction means reconstructs a plurality of sagittal images that are adjacent to each other from the three-dimensional image.

9. A medical image management apparatus, as defined in claim 1, wherein when the subject is a human body, and the predetermined direction is an axial direction, if the information obtained by the information obtainment means represents the torso of the subject, or at least one of the urinary organs of the subject, or the pituitary gland of the subject, the reconstruction means reconstructs a plurality of coronal images or sagittal images that are adjacent to each other from the three-dimensional image.

10. A medical image management apparatus, as defined in claim 1, wherein the information obtainment means automatically obtains the information representing the region by performing image analysis on the three-dimensional image or at least one of the slice images composing the three-dimensional image.

11. A medical image management apparatus, as defined in claim 1, wherein the information obtainment means automatically obtains the information representing the region based on subject information provided, as supplementary information, for at least one of the slice images composing the three-dimensional image.

12. A medical image management system comprising:
the medical image management apparatus, as defined in claim 1; and
the external terminal, as defined in claim 1, wherein the external terminal includes a sending/receiving means that outputs a distribution request for the three-dimensional image t the medical image management apparatus and sequentially receives a plurality of slice images distributed from the medical image management apparatus, an image display means for displaying an image, and a display control means that displays, as an initial image, one of the plurality of slice images received by the sending/receiving means on the image display means.

13. A medical image management method for managing images of a subject that has been imaged by a medical image imaging apparatus, the method comprising the steps of:
recording each region of the subject which is a target of imaging by the medical image imaging apparatus, correlated with a direction for reconstruction;
obtaining information representing a region of the subject represented in a three-dimensional image constructed based on a plurality of slice images that have been captured by the medical image imaging apparatus, the plurality of slice images being adjacent to each other in a predetermined direction;
reconstructing the plurality of slice images which are adjacent in the predetermined direction, into a plurality of slice images which are adjacent in a direction correlated with the region of the subject represented by the obtained information prior to a request for distribution of the three-dimensional image being received from an external terminal;
recording the plurality of reconstructed slice images; and
sequentially distributing, in response to a distribution request for the three-dimensional image input from an external terminal, the plurality of reconstructed and recorded slice images to the external terminal.

14. A medical image management method, as defined in claim 13, wherein when the position of a lesion in the three-dimensional image has been correlated with the three-dimensional image, priority is given to distribution of a reconstructed slice image including the position of the lesion over distribution of the other slice images of the plurality of reconstructed slice images.

15. A medical image management method, as defined in claim 13, wherein when a reading report that records a specific position in the three-dimensional image has been correlated with the three-dimensional image, priority is given to distribution of a reconstructed slice image including the specific position over distribution of the other slice images of the plurality of reconstructed slice images.

16. A medical image management method, as defined in claim 13, wherein with respect to a plurality of three-dimensional images obtained by imaging the same region of the subject at a plurality of different points of time, information representing a region of the subject represented in the plurality of three-dimensional images is obtained, and wherein a plurality of slice images that are adjacent to each other in a direction that has been correlated with the region in advance are reconstructed from each of the plurality of three-dimensional images based on the obtained information representing the region, and wherein the plurality of reconstructed slice images are sequentially distributed, based on a distribution request for the plurality of three-dimensional images, in such a manner that slice images representing the same slice plane in the plurality of three-dimensional images are distributed together.

17. A medical image management method, as defined in claim 16, wherein when the position of a lesion in at least one of the plurality of three-dimensional images has been correlated with the at least one of the plurality of three-dimensional images, priority is given to distribution of a reconstructed slice image including the position of the lesion over distribution of the other slice images of the plurality of reconstructed slice images.

18. A recording medium stored therein a medical image management program for managing images of a subject that has been imaged by a medical image imaging apparatus, the program causing a computer to execute the procedures of:
recording each region of the subject which is a target of imaging by the medical image imaging apparatus, correlated with a direction for reconstruction;
obtaining information representing a region of the subject represented in a three-dimensional image constructed based on a plurality of slice images that have been captured by the medical image imaging apparatus, the plurality of slice images being adjacent to each other in a predetermined direction;

reconstructing the plurality of slice images which are adjacent in the predetermined direction, into a plurality of slice images which are adjacent in a direction correlated with the region of the subject represented by the obtained information prior to a request for distribution of the three dimensional image being received from an external terminal;

recording the plurality of reconstructed slice images; and sequentially distributing, in response to a distribution request for the three-dimensional image input from an external terminal, the plurality of reconstructed and recorded slice images to the external terminal.

19. A recording medium stored therein a medical image management program, as defined in claim 18, wherein when the position of a lesion in the three-dimensional image has been correlated with the three-dimensional image, priority is given to distribution of a reconstructed slice image including the position of the lesion over distribution of the other slice images of the plurality of reconstructed slice images.

20. A recording medium stored therein a medical image management program, as defined in claim 18, wherein with respect to a plurality of three-dimensional images obtained by imaging the same region of the subject at a plurality of different points of time, information representing a region of the subject represented in the plurality of three dimensional images is obtained, and wherein a plurality of slice images that are adjacent to each other in a direction that has been correlated with the region in advance are reconstructed from each of the plurality of three-dimensional images based on the obtained information representing the region, and wherein the plurality of reconstructed slice images are sequentially distributed, based on a distribution request for the plurality of three-dimensional images, in such a manner that slice images representing the same slice plane in the plurality of three-dimensional images are distributed together.

* * * * *